United States Patent [19]

Righelato et al.

[11] 4,110,162
[45] Aug. 29, 1978

[54] PRODUCTION OF A POLYSACCHARIDE UNDER CARBON LIMITING CONDITIONS

[75] Inventors: Renton Clive Righelato; Trevor Rodney Jarman, both of Reading, England

[73] Assignee: Tate & Lyle Limited, London, England

[21] Appl. No.: 798,761

[22] Filed: May 20, 1977

[30] Foreign Application Priority Data

May 28, 1976 [GB] United Kingdom ............... 22319/76

[51] Int. Cl.$^2$ .......................................... C12D 13/04
[52] U.S. Cl. ..................................... 195/31 P; 195/96
[58] Field of Search .......................... 195/31 P, 115, 96

[56] References Cited

U.S. PATENT DOCUMENTS

| 2,822,319 | 2/1958 | Monod | 195/115 |
| 3,856,625 | 12/1974 | Imrie | 195/31 P |

FOREIGN PATENT DOCUMENTS 1,331,771  9/1973  United Kingdom .................. 195/31 P

OTHER PUBLICATIONS

Neijssel et al., "The Regulation of Carbohydrate Metabolism in Klebsiella aerogens NCTC418 Organisms, Growing in Chemostat Culture", Arch. Microbiol., vol. 106, (1975) pp. 251–258.

Lopez et al., "Polysaccharide Production by Beijerinckia and Azolobacter.", Chem. Abstracts, vol. 71, No. 13, p. 130, (1969), abs. No. 57950e.

Holme, "Glycogen Formation in Continuous Culture of Escherichia coli B", Continuous Cultivation of Microorganisms a Symposium, Prague, 1958, pp. 1–8.

*Primary Examiner*—Raymond N. Jones
*Assistant Examiner*—Thomas G. Wiseman
*Attorney, Agent, or Firm*—Ostrolenk, Faber, Gerb & Soffen

[57] ABSTRACT

Polysaccharide is produced in good yields with good control by continuous culture of a polysaccharide-producing strain of *Azotobacter vinelandii* under carbon-limited conditions, preferably with restricted oxygen uptake, with the advantage that the effluents produced are non-polluting having a low biological oxygen demand (B.O.D.).

6 Claims, No Drawings

PRODUCTION OF A POLYSACCHARIDE UNDER CARBON LIMITING CONDITIONS

This invention relates to a process for the production of a polysaccharide. More particularly the invention relates to the production of an alginate-type polysaccharide by the cultivation of bacteria of the species *Azotobacter vinelandii*.

Alginic acid, a hydrophilic colloidal carbohydrate acid, is a variable block copolymer composed of D-mannuronic and L-guluronic acid units. Although alginic acid itself is practically insoluble in water, it can readily be solubilised by neutralisation with a suitable alkali. One of the outstanding characteristics of alginate solutions is their high viscosity at very low concentrations; and when certain divalent ions, such as calcium or magnesium, are added to solutions of alginate, gelation is induced. The unique physical properties of alginic acid and alginates give them a wide range of industrial applications as emulsifiers, stabilisers and thickeners.

Alginates and alginic acid have been obtained on a commercial scale by extraction of certain species of brown seaweed, for example *Laminaria digitata* and *Ascophyllum nodosum*, in which they make up a large proportion of the cell walls.

This conventional seaweed extraction process suffers from the disadvantage of being dependent on the supply of alginate-containing seaweed as starting material. It is awkward to carry out because of the quantities of seaweed involved; and considerable further purification may be necessary, especially if food or pharmaceutical grade material is required.

In view of these difficulties, in recent years alginate-like polysaccharides have been produced by cultivation of several species of *Azotobacter*, in particular *Azotobacter vinelandii*. The alginic acid produced by this microorganism is structurally similar to that obtained from seaweed, except that it is partially acetylated.

It is known that the production of polysaccharide using a strain of *Azotobacter vinelandii* is critically dependent on a number of factors, particularly the pH of the medium and also the level of phosphate in the medium.

In U.K. Patent specification No. 1,331,771, there is described and claimed a process for the production of a polysaccharide which comprises cultivating a microorganism of the species *Azotobacter vinelandii* under aerobic conditions in an aqueous nutrient medium containing at least one monosaccharide and/or disaccharide as carbon source and containing as essential ingredients sources of molybdenum, iron, phosphate, magnesium, potassium, sodium, calcium and sulphate, under controlled pH conditions, such that the pH is maintained in the range of from 6.5 to 8.5 for at least the first half of the fermentation period and within the range of from 4.5 to 8.5 for the remainder of the fermentation period, if any, until a substantial formation of polysaccharide has occurred, and isolating the polysaccharide formed. The method of culture used in this process can be batch or continuous culture.

In U.K. Patent specification No. 1,394,413, a special selection of these conditions is described giving particularly good polysaccharide yields. In this Specification, a process similar to that of the earlier Specification is described and claimed, but limited in that the concentration of phosphate in the medium is from 0.1 to 0.8 millimolar, and that during the cultivation the pH of the medium is maintained within the range of 7.0 to 8.2.

U.K. Patent specification No. 1,394,413 again stresses that best results are obtained at low phosphate concentrations. Under continuous culture conditions, one component of the medium will always be limiting on the growth of the microorganism: all other nutrients being provided in excess. At low phosphate levels, the phosphate itself may be limiting substrate, depending on the availability of other nutrients.

The sugar, whether monosaccharide or disaccharide, used in the culture medium is the source from which the polysaccharide product is constructed. Thus in conventional practice, whether batch or continuous, an unrestricted supply of sugar is supplied to the microorganisms, so as to maximise the yield of polysaccharide obtained, any shortage of sugar being regarded as harmful to the overall yield. The excess of sugar, unused by the microorganism, remains in the culture medium after the cells and polysaccharide have been removed. This process is, of course, wasteful of sugar resources, but also causes serious pollution problems when the effluent is assimilated in water sources such as rivers or lakes. The excess of sugar causes the effluent to have a high biological oxygen demand (B.O.D.), thus resulting in deoxygenation of the water into which it flows, with consequent harm to animal and plant life. However, any attempt to restrict the supply of sugar in a continuous fermentation of this type causes serious problems as the system becomes very unstable and is difficult to control.

Most surprisingly we have now discovered that if the supply of sugar to a continuous fermentation system is actually restricted so much that the sugar becomes the growth-limiting constituent of the medium, the yield of polysaccharide is good and the system is stable and easy to control, while the effluent is substantially free of sugar and consequently has a very much lower B.O.D.

According to the present invention therefore, there is provided a process for the production of a polysaccharide consisting of a partially acetylated variable block copolymer of 1-4 linked D-mannuronic and L-guluronic acid residues, which comprises subjecting to continuous cultivation a bacterium of the species *Azotobacter vinelandii* under aerobic conditions in an aqueous culture medium containing as essential ingredients at least one monosaccharide or disaccharide as carbon source and sources of phosphate, molybdenum, iron, magnesium, potassium, sodium, calcium and sulphate, said medium containing a fixed source of nitrogen and/or the aerating gas containing nitrogen, the concentration of the saccharide carbon source in the medium being limiting on the growth of the bacterium, and during the cultivation the pH in the medium being maintained within the range of 6.0 to 8.2.

Any strain of *Azotobacter vinelandii* can be used in the process of the present invention. However, particularly valuable strains which give especially good yields of the polysaccharide is that particularly mentioned in the two earlier Specifications and bearing the culture collection numbers NCIB 9068 and NCIB 8789, and that bearing the culture collection number NCIB 8660. These strains are available from the National Collection of Industrial Bacteria, Torry Research Station, P.O. Box 31, 135 Abbey Road, Aberdeen, Scotland, and are described in the catalogue of the collection.

The level of monosaccharide or dissaccharide carbon source used in the medium will vary depending on the cell concentration in the fermenter: the higher the cell concentration, the higher the level of saccharide which is limiting. We have found, for example, that using a chemically defined medium of the type mentioned in Example 1 of Specification No. 1,331,771, a sucrose concentration of 24 mM is effectively limiting at a cell concentration of about 1.3 g/l, when the respiration rate is approximately 16 m moles oxygen/g cell/hour. Similarly, a sucrose concentration of 240 mM is effectively limiting at a cell concentration of about 13.6 g/l and a respiration rate of about 5 m moles oxygen/g cell/hour. These results are obtained at dilution rates of 0.15 and 0.05 $h^{-1}$ respectively.

In any particular case, an indication of whether the sucrose (or other mono- or disaccharide) concentration is truly limiting can be obtained by increasing the sucrose concentration and observing the effect on the cell concentration. If the concentration of a non-limiting component of the medium is raised, no significant change in the cell concentration is observed; however, if the concentration of the limiting component is raised, the cell concentration rapidly responds by increasing.

We have found that under conventional continuous culture conditions, for example those using a chemostat (see Herbert, Elsworth and Telling, 1956, Journal of General Microbiology, 14, 601), particularly advantageous sucrose levels are as high as 240 millimolar, but no upper limit to the sucrose concentration can be set, except that dictated by the practical considerations governing the continuous fermentation process.

Whatever the level of sucrose in the medium, however, provided it is truly limiting on the growth of the A. vinelandii, the effluent is substantially free of residual sugar. Furthermore, the sugar level in the culture medium itself is easily controlled at a stable level, since it is in effect the microorganism itself which is acting as the controlling agent.

Of the various mono- and disaccharides suitable as carbon sources in the production of polysaccharide by Azotobacter vinelandii, we have found that sucrose is preferable.

Apart from the use of limiting conditions for the monosaccharide or disaccharide carbon source, the medium can otherwise contain any of the usual components used in the production of polysaccharide from Azotobacter vinelandii.

We have, however, found that the rate of oxygen supply is related to the efficiency with which the monosaccharide or disaccharide carbon source is converted into polysaccharide. In continuous culture conditions, it is the relationship of the oxygen level to the cell concentration which is critical and not the oxygen concentration in the medium as such. High oxygen levels promote the respiration of the microorganism, thus converting the sucrose (or other carbon source) into carbon dioxide. On the other hand, oxygen-limiting conditions restrict the formation of polysaccharide. Careful control of the oxygen supply, can however, give a sucrose conversion figure of about 30% or even over 40%, thus providing a much more efficient utilisation of the carbon source. Typically the oxygen uptake is restricted to from 5 to 20 m moles $O_2$/h/g cell.

The actual uptake of oxygen in millimoles per liter per hour corresponding to these figures will, of course, depend on the cell concentration in the fermenter. The uptake per liter per hour is generally within the ranges stated in the earlier Specifications, but it must be emphasised that it is the relationship of the oxygen supply to the cell concentration which is important.

Alteration of the supply of oxygen to the culture can be effected by various means. Firstly, the concentration of oxygen in the gas, usually air, which is passed into the culture during fermentation, can be altered by diluting the air with nitrogen or an inert gas, or by enriching the air with extra oxygen. Secondly, the pressure of the gas being passed into the culture can be altered so that the rate of dissolution is reduced. Thirdly, the efficiency with which the oxygen in the gas phase is transferred into the aqueous phase can be altered by altering the gas-liquid mixing characteristics, conveniently by altering the speed and efficiency of the stirrer. A combination of two or more of these methods can also be used to provide the correct balance of nitrogen and oxygen.

The following Examples illustrate the invention further.

EXAMPLE 1

ALGINATE PRODUCTION UNDER CARBON-LIMITING CONDITIONS IN CONTINUOUS CULTURE

Azotobacter vinelandii NCIB 9068 was grown continuously in a continuous culture of the chemostat type (Herbert, Elsworth and Telling 1956, Journal of General Microbiology, 14, 601) using Azotobacter vinelandii NCIB 9068 in a continuous culture apparatus with a culture volume of 1.0 liters, with the phosphate decreased to the concentrations stated. The medium was pumped into the culture at 150 ml/hr and the culture broth over-flowed via a standpipe weir into a receiver vessel. The temperature was controlled at 30° C. The pH was controlled at 7.4 by automatic addition of 1 M NaOH. Air was sparged into the fermenter at 1 liter/min, the impeller speed being adjusted so that oxygen uptake rates in the range 10–30 m moles/g cell/hour were obtained. Samples were taken from the fermenter at daily intervals and assayed for cell mass and polysaccharide concentration. To each 40 ml sample, 0.8 ml of 0.5 M EDTA plus 0.8 ml of 5 M NaCl was added. The samples were then centrifuged at 25,000 g for 40 mins. The cell pellet obtained was resuspended in distilled water, centrifuged at 25,000 g for 40 mins and the supernatant decanted. The pre-weighed tube containing the sediment was dried at 105° C. for 12 hours and weighed. The polysaccharide was precipitated from the supernatant of the first centrifugation by adding three volumes of propan-2-ol. The precipitate was collected by filtration, dried in vacuo at 45° C. for 24 hours and weighed.

The culture medium, the final composition of which is given in Table 1, was prepared and added to the culture in two batches. Batch (1) was autoclaved at 1 kg/cm² for 1 hour in two parts which were combined aseptically after cooling. One part contained sucrose, $KH_2PO_4$ and $K_2HPO_4$ in 14 l, the other part contained $MgSO_4$, NaCl and trace elements other than Ca and Fe in 4 l. Batch (2) contained $CaCl_2$ and $FeCl_2$ in 2 l; the $CaCl_2$ was autoclaved in 1.9 l and the $FeCl_2$ was filter sterilised and then added to the bulk of Batch (2). Batches (1) and (2) were added to the culture through separate lines, (1) being added at a rate of 135 ml/h, and (2) at 15 ml/h.

Carbon limitation was demonstrated by increasing the sucrose concentration in the medium to 40 g/l: within five hours, the cell concentration increased by more than 10%. The level of sucrose was determined by g.l.c.

The amount of polysaccharide produced per g cell under carbon limitation and the amount of residual sucrose are shown in Table 2. For comparison, the residual sucrose level under conventional conditions in which sucrose is not the limiting nutrient may be as high as 10 mM or 15 mM.

EXAMPLE 2

Using the medium shown in Table 1, a sugar level 10 times that of Example 1 was growth-limiting at a dilution rate of 0.05 h$^{-1}$. The residual sugar was negligible but a polysaccharide concentration of 20 g/l was obtaind in 25% conversion efficiency.

EXAMPLE 3

This example shows the effect of not restricting the oxygen uptake. At a respiration rate of 28 m moles $O_2$/h/g cell (as opposed to 16 and 5.2 m moles $O_2$/h/g cell respectively in Examples 1 and 2), the conversion efficiency dropped to 14%.

However, the example does show that aerial nitrogen can at least in part be replaced by a fixed nitrogen source.

TABLE 1

CULTURE MEDIA

| CONSTITUENT | AMOUNT ADDED (g/l culture medium) | | |
|---|---|---|---|
| | EXAMPLE 1 | EXAMPLE 2 | EXAMPLE 3 |
| Sucrose | 8 | 80 | 4 |
| | (=24mM) | (=240mM) | (=12mM) |
| $KH_2PO_4$ | 0.064 | 0.096 | 0.032 |
| $K_2HPO_4$ | 0.25 | 0.375 | 0.12 |
| $MgSO_4 \cdot 7H_2O$ | 1.6 | 1.6 | 0.2 |
| NaCl | 1.6 | 1.6 | 0.2 |
| $Na_2MoO_4$ | 0.008 | 0.008 | 0.001 |
| $CaCl_2 \cdot 2H_2O$ | 0.34 | 0.34 | 0.043 |
| $FeCl_2 \cdot 2H_2O$ | 0.017 | 0.25 | 0.002 |
| $H_3BO_4$ | $23 \times 10^{-3}$ | $23 \times 10^{-3}$ | $2.9 \times 10^{-3}$ |
| $CoSO_4 \cdot 7H_2O$ | $9 \times 10^{-3}$ | $9 \times 10^{-3}$ | $1.2 \times 10^{-3}$ |
| $MnCl_2 \cdot 4H_2O$ | $0.7 \times 10^{-3}$ | $0.7 \times 10^{-3}$ | $0.09 \times 10^{-3}$ |
| $ZnSO_4 \cdot 7H_2O$ | $9 \times 10^{-3}$ | $9 \times 10^{-3}$ | $1.2 \times 10^{-3}$ |
| $CuSO_4 \cdot 7H_2O$ | $0.8 \times 10^{-3}$ | $0.8 \times 10^{-3}$ | $0.1 \times 10^{-3}$ |
| $(NH_4)_2SO_4$ | — | — | 1.0 |

TABLE 2

ALGINATE PRODUCTION UNDER CARBON-LIMITING CONDITIONS IN CONTINUOUS CULTURE

| | Example 1 | Example 2 | Example 3 |
|---|---|---|---|
| Concentration of limiting substrate in culture medium (mM) | 24 | 240 | 12 |
| Cell concentration (g/l) | 1.3 | 13.6 | 0.9 |
| Respiration Rate (m moles $O_2$/h/g cell) | 16 | 5.2 | 28 |
| Polysaccharide concentration (g/l) | 2.2 | 20 | 0.56 |
| Conversion efficiency (%) (utilised substrate into polysaccharide produced) | 28 | 25 | 14 |
| Residual sucrose in culture medium (mM) | 0.5 | 0 | 0 |
| Polysaccharide yield per g cell (g) | 1.7 | 1.47 | 0.62 |
| Dilution rate (h$^{-1}$) | 0.15 | 0.05 | 0.15 |
| Productivity = Polysaccharide concentration & Dilution Rate (g/l/h) | 0.33 | 1.0 | 0.08 |

We claim:

1. In a process for the production of a polysaccharide comprising subjecting to continuous cultivation a bacterium of the species *Azotobacter vinelandii* under aerobic conditions in an aqueous culture medium containing as essential ingredients at least one monosaccharide or disaccharide as carbon source and sources of phosphate, molybdenum, iron, magnesium, potassium, sodium, calcium and sulphate, said medium containing a source of nitrogen selected from the group consisting of a fixed source of nitrogen and gaseous nitrogen, oxygen being supplied during cultivation, the pH in the medium during cultivation being maintained within the range of about 6.0, to about 8.2 and recovering said polysaccharide, the improvement comprising maintaining the concentration of the saccharide carbon source in the medium so that it is limiting the growth nutrient.

2. The process of claim 1, wherein the *A. vinelandii* strain used is selected from the group consisting of strains NCIB 9068, 8789 and 8660.

3. The process of claim 1, wherein sucrose is used as the carbon source.

4. The process of claim 3, wherein the sucrose is used at a concentration of from about 24 to about 240 mM.

5. The process of claim 1, wherein oxygen is supplied at a rate which is restricted within a range giving optimum conversion to polysaccharide.

6. The process of claim 5, wherein the oxygen uptake is from about 5 to about 20 m moles $O_2$/h/g cell.

* * * * *